United States Patent
Springer et al.

(10) Patent No.: US 7,342,135 B2
(45) Date of Patent: Mar. 11, 2008

(54) 3(4),7(8)-BIS(AMINOMETHYL)BICYCLO [4.3.0]NONANE AND A PROCESS FOR ITS PREPARATION

(75) Inventors: Helmut Springer, Dinslaken (DE); Paolo Bavaj, Frankfurt (DE)

(73) Assignee: Celanese Chemicals Europe GmbH, Oberhausen (DE)

( * ) Notice: Subject to any disclaimer, the term of this patent is extended or adjusted under 35 U.S.C. 154(b) by 0 days.

(21) Appl. No.: 11/657,749

(22) Filed: Jan. 25, 2007

(65) Prior Publication Data

US 2007/0179319 A1  Aug. 2, 2007

(30) Foreign Application Priority Data

Jan. 31, 2006  (DE) .................. 10 2006 004 324

(51) Int. Cl.
  *C07C 209/60*  (2006.01)
  *C07C 211/36*  (2006.01)
  *C07C 211/38*  (2006.01)

(52) U.S. Cl. .................. 564/446; 564/448; 564/456
(58) Field of Classification Search ................ None
See application file for complete search history.

(56) References Cited

U.S. PATENT DOCUMENTS

| | | | | |
|---|---|---|---|---|
| 3,228,984 A | * | 1/1966 | Humber | 564/306 |
| 3,317,387 A | * | 5/1967 | Prichard | 514/210.01 |
| 3,525,770 A | * | 8/1970 | Chow | 564/456 |
| 4,500,469 A | * | 2/1985 | Simon et al. | 562/14 |

* cited by examiner

*Primary Examiner*—Brian Davis
(74) *Attorney, Agent, or Firm*—Charles A. Muserlian

(57) ABSTRACT

3(4),7(8)-bis(aminomethyl)bicyclo[4.3.0]nonane and a process for its preparation, wherein bicyclo[4.3.0]nona-3,7-diene is reacted with synthesis gas in a homogeneous organic phase in the presence of transition metal compounds of Group VIII of the Periodic Table containing complex-bound organophosphorus compounds, and excess organophosphorus compound, at temperatures of 70 to 160° C. and pressures of 5 to 35 MPa, and the 3(4),7(8)-bisformylbicyclo [4.3.0]nonane thus obtained is reductively aminated.

15 Claims, No Drawings

3(4),7(8)-BIS(AMINOMETHYL)BICYCLO [4.3.0]NONANE AND A PROCESS FOR ITS PREPARATION

The present invention relates to the chemical compound, 3(4),7(8)-bis(aminomethyl)bicyclo[4.3.0]nonane and to a process for its preparation from bicyclo[4.3.0]nona-3,7-diene.

STATE OF THE ART

Fused alicyclic unsaturated hydrocarbons with isolated double bonds in the rings are valuable starting materials which can be converted to compounds with important uses. The cyclic and fused hydrocarbon skeleton imparts particular properties. One example of this compound class is dicyclopentadiene (DCP), which is readily available by dimerizing cyclopentadiene and is also prepared on the industrial scale, and can be converted to compounds with important uses, to which the tricyclodecane skeleton imparts particular properties. The compounds which are derived from DCP and have a tricyclodecane structure are frequently also referred to in the literature as TCD derivatives (Chemiker-Zeitung, 98, 1974, pages 70 to 76).

Especially the hydroformylation of DCP affords TCD aldehydes of interest, such as 3(4),8(9)-bisformyltricyclo[5.2.1.0$^{2,6}$]decane, also known as TCD dialdehyde, which is processed further to give important intermediates. Owing to its thermal lability, which leads to losses in the course of distillative workup, TCD dialdehyde is usually not isolated in pure form but rather processed further as the crude product of the hydroformylation reaction. For instance, the reductive amination of TCD dialdehyde leads to TCD diamine{3(4),8(9)bis(aminomethyl)tricyclo[5.2.1.0$^{2,6}$]decane}, which finds use as a valuable intermediate in numerous industrially practiced syntheses, for example for the preparation of light-resistant polyurethane systems according to DE 28 19 980 A1, for producing dental materials (WO 2002/013767 A2, EP 678 533 A2), for the synthesis of polyamides (EP 168 816 A2), polyfunctional epoxy resin systems (JP 58 135 875 A), heat-curable coating materials (EP 59 962 A1), of epoxy resin hardeners (JP 54 004 992 A) and for preparing TCD diisocyanate (NL 66 14 717 A).

The preparation of aldehydes by catalytic addition of carbon monoxide and hydrogen of olefinic double bonds is known. While this reaction used to be performed virtually exclusively with cobalt as the catalyst, modern processes work with metallic rhodium or with rhodium compounds as catalysts, which are used alone or with complexing ligaments, for example organophosphines or esters of phosphorous acid. According to the unanimous opinion in the technical field, catalysts effective under the reaction conditions are hydrido carbonyl compounds of rhodium which can be reproduced by the formula H[Rh(CO)$_{4-x}$L$_x$] where L is a ligand and x is 0 or an integer from 1 to 3.

A special case is the hydroformylation of dienes. While almost exclusively monoaldehydes are obtained under the customary conditions of the oxo process in the hydroformylation of conjugated dienes, it is possible to obtain not only the mono- but also the disubstitution products from dicyclopentadiene (DCP) with its isolated double bonds. Owing to the great significance of the hydroformylation products of DCP, there are also numerous studies in the technical literature which address both the hydroformylation reaction of DCP and the subsequent workup of the crude product. For instance, DE 38 22 038 A1 and GB 1 170 226 consider the hydroformylation of DCP in the presence of rhodium in an organic solvent at elevated pressure and elevated temperature. A comprehensive review of the hydroformylation of dicyclopentadiene can be found in the Chemiker-Zeitung 98, 1974, 70-76, where reference is likewise made to the thermal lability of the TCD aldehydes, which leads to high product losses in the distillative workup of the crude hydroformylation mixture.

Therefore, TCD dialdehydes are usually not isolated in pure form but processed further in their mixtures with the by-products of the oxo process. However, indications of extractive workup processes without thermal stress can also be found in the prior art, for example in EP-1 065 194 A1 or U.S. Pat. No. 5,138,101 A. In these processes, the organic crude mixture is extracted with a polar organic solvent, for example with a polyhydric alcohol or with a methanol/water mixture, which transfers the TCD dialdehydes to the polar alcoholic phase, and the hydroformylation catalyst remains in the hydrocarbon phase.

The preparation of TCD diamine is known from DE 38 22 038 A1. According to this, dicyclopentadiene is hydroformylated in organic solution in the presence of rhodium to give the crude TCD dialdehyde, which is subsequently reductively aminated without further removal of the TCD dialdehyde and without removal of the catalyst in a second reaction step in the presence of a primary amine.

According to JP 10 087 573A, TCD diamine is prepared by hydrogenating the corresponding TCD dialdehyde dioxime in the presence of Fe—Cr-modified Raney nickel. Owing to the great economic significance that aminomethylated diamines based on fused, alicyclic hydrocarbons have, there is therefore a need for the provision of further, inexpensively available aminomethylated diamines in high purity, which have a cyclic hydrocarbon skeleton with fused rings.

OBJECTS OF THE INVENTION

It is an object of the invention to provide the novel compound, 3(4),7(8)-bis(aminomethyl)bicyclo[4.3.0] nonane.

It is another object of the invention to provide a novel process for the preparation of the novel nonane.

These and other objects and advantages of the invention will become obvious from the following detailed description.

THE INVENTION

The process of the invention for preparing 3(4),7(8)-bis (aminomethyl)bicyclo[4.3.0]nonane by hydroformylating bicyclo[4.3.0]nona-3,7-diene followed with subsequent reductive amination. It comprises reacting bicyclo[4.3.0] nona-3,7-diene with synthesis gas in a homogeneous organic phase in the presence of transition metal compounds of Group VIII of the Periodic Table containing complex-bound organophosphorus compounds, and excess organophosphorus compound, at temperatures of 70 to 160° C. and pressures of 5 to 35 MPa, and then reductively aminating the 3(4),7(8)-bisformylbicyclo[4.3.0]nonane thus obtained to form 3(4),7(8)-bis(aminomethyl)bicyclo[4.3.0]nonane.

The inventive compound derives from bicyclo[4.3.0] nona-3,7-diene, which is prepared industrially by Diels-Alder reaction of butadiene with cyclopentadiene and which is therefore available in inexpensive amounts.

The numbering of the carbon atoms bonded in the unsaturated, bicyclic hydrocarbon is according to the following formulae:

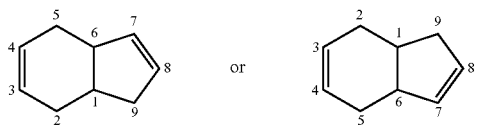

the two structural formulae being identical.

The inventive compound, 3(4),7(8)-bis(aminomethyl)bicyclo[4.3.0]nonane, is a mixture of different isomers of bis(aminomethyl)bicyclo[4.3.0]nonane in which the aminomethyl group in the six-membered ring can be bonded once at the 3- or at the 4-position, and the aminomethyl group in the five-membered ring once at the 7- or at the 8-position.

In analogy to the notation customary for the TCD derivatives according to Chemiker-Zeitung, 98, 1974 pages 70 to 76, the inventive compound 3(4),7(8)-bis(aminomethyl)bicyclo[4.3.0]nonane can be described in terms of formula as follows:

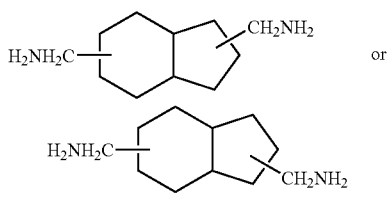

the two structural formulae being identical.

The starting material, bicyclo[4.3.0]nona-3,7-diene, can be supplied to the hydroformylation as such or in solution. Suitable solvents are those in which starting material, reaction product and catalyst are soluble and which behave inertly under the reaction conditions, for example water-insoluble ketones, dialkyl ethers, aliphatic nitriles, aromatic hydrocarbons such as benzene, toluene, the isomeric xylenes or mesitylene, and saturated cycloaliphatic hydrocarbons such as cyclopentane or cyclohexane, or saturated aliphatic hydrocarbons such as n-hexane, n-heptane or n-octane. The proportion of the solvent in the reaction medium can be varied over a wide range and is typically from 10 to 80% by weight, preferably from 20 to 50% by weight, based on the reaction mixture.

The hydroformylation stage is performed in a homogeneous reaction system. The term homogeneous reaction system represents a homogeneous solution composed essentially of solvent, if added in the reaction stage, catalyst, excess organophosphorus compound, unconverted starting compound and hydroformylation product.

The catalysts used are transition metal compounds of Group VIII of the Periodic Table which contain complex-bound organophosphorus compounds. Preference is given to using complexes of cobalt, rhodium, iridium, nickel, iron, platinum, palladium or ruthenium, and especially of cobalt, rhodium and iridium. Particular preference is given to the use of rhodium complexes which contain organic phosphorus (III) compounds as ligands. Such complexes and their preparation are known (for example from U.S. Pat. No. 3,527,809 A, U.S. Pat. No. 4,148,830 A, U.S. Pat. No. 4,247,486 A and U.S. Pat. No. 4,283,562 A). They may be used as homogeneous complexes or else as a mixture of different complexes.

The rhodium concentration in the reaction medium extends over a range of 5 to 1000 ppm by weight and is preferably 10 to 700 ppm by weight. In particular, rhodium is employed in concentrations of 20 to 500 ppm by weight, based in each case on the homogeneous reaction mixture.

The hydroformylation is performed in the presence of a catalyst system composed of rhodium-organophosphorus complex and free, i.e. excess, organophosphorus ligand which does not enter into a complex with rhodium. The free organophosphorus ligand may be the same as in the rhodium complex, but it is also possible to use different ligands. The free ligand may be a homogeneous compound or consist of a mixture of different organophosphorus compounds.

Examples of rhodium-organophosphorus complexes which may find use as catalysts are described in U.S. Pat. No. 3,527,809 A. The preferred ligands in the rhodium complex catalysts include, for example, triarylphosphines such as triphenylphosphine, trialkylphosphines such as tri(n-octyl)phosphine, trilaurylphosphine, tri(cyclohexyl)phosphine, alkylarylphosphines, alkyl phosphites, aryl phosphites, alkyl diphosphites and aryl diphosphites. For instance, it is likewise possible to use rhodium complexes which contain aryl phosphites of the formula $P(OR^1)(OR^2)(OR^3)$ in complex-bound form, where at least one of $R^1$, $R^2$ or $R^3$ groups is an ortho-substituted phenyl ring. Suitable complex ligands have been found to be tris(2-tert-butylphenyl)phosphite or tris(2-tert-butyl-4-methylphenyl)phosphite. The rhodium-catalyzed hydroformylation of olefins with phosphite-modified complexes is known from EP 0 054 986 A1. Owing to its easy availability, triphenylphosphine is employed particularly frequently.

Typically, the molar ratio of rhodium to phosphorus in the homogeneous reaction mixture is 1:5 to 1:200, but the molar proportion of the phosphorus in the form of organic phosphorus compounds may also be higher. Preference is given to using rhodium and organically bound phosphorous in molar ratios of 1:10 to 1:100.

When a transition metal of Group VIII of the Periodic Table other than rhodium is used in the hydroformylation stage, the concentration of transition metal and the molar ratio of transition metal to phosphorus is within the ranges which are also selected for rhodium. The optimal values in each case can be determined by simple routine tests depending on the transition metal used in each case.

The conditions under which the hydroformylation proceeds can vary within wide limits and can be adjusted to the individual circumstances. They depend upon factors including the starting material, the catalyst system used and the desired conversion. Typically, the hydroformylation of bicyclo[4.3.0]nona-3,7-diene is performed at temperatures of 70 to 160° C. Preference is given to maintaining temperatures of 80 to 150° C. and in particular 90 to 140° C. The total pressure extends over a range of 5 to 35 MPa, preferably 10 to 30 MPa and in particular 20 to 30 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The catalyst is typically formed from the transition metal or transition metal compound, organophosphorus compound and synthesis gas under the conditions of the hydroformylation reaction in the reaction mixture. However, it is also possible first to preform the catalyst and then to feed it to the actual hydroformylation stage. The conditions of the preformation correspond generally to the hydroformylation conditions.

For the preparation of the hydroformylation catalyst, the transition metal of Group VIII of the Periodic Table, especially rhodium, is used either in metallic form or as a compound. In metallic form, the transition metal is used either in the form of fine particles or in a thin layer on a support, such as activated carbon, calcium carbonate, aluminium silicate, alumina.

Suitable transition metal compounds are salts of aliphatic mono- and polycarboxylic acids such as transition metal 2-ethylhexanoates, acetates, oxalates, propionates or malonates. In addition, it is possible to use salts of inorganic hydrogen and oxygen acids such as nitrates or sulfates, the various transition metal oxides or else transition metal carbonyl compounds such as $Rh_3(CO)_{12}$, $Rh_6(CO)_{16}$, $Co_2(CO)_8$, $Co_4(CO)_{16}$, $Fe(CO)_5$, $Fe_2(CO)_9$, $Ir_2(CO)_8$, $Ir_4(CO)_{12}$ or transition metal complexes, for example cyclopentadienylrhodium compounds, rhodium acetylacetonate, cyclopentadienylcobalt(cyclooctodiene-1,5), $Fe(CO)_3$(cyclooctadiene-1,5), [RhCl(cyclooctadiene-1,5]$_2$ or $PtCl_2$(cyclooctadiene-1,5). Transition metal-halogen compounds are less useful owing to their corrosive behavior of the halide ions.

Preference is given to transition metal oxides and in particular, transition metal acetates and 2-ethylhexanoates. Particular suitable compounds have been found to be rhodium oxide, rhodium acetate, rhodium 2-ethyl-hexanoate, cobalt oxide, cobalt acetate and cobalt 2-ethylhexanoate.

The hydroformylation stage may be performed either batchwise or continuously. In the process of the invention, the starting olefin bicyclo[4.3.0]nona-3,7-diene is converted virtually completely, and a crude hydroformylation product having a content of the desired bisformyl product which is usually above 75% by weight, based on the crude hydroformylation product is obtained.

The reaction product of the hydroformylation stage is reductively aminated without further purification and without catalyst removal.

Reductive amination is understood to mean the reaction of 3(4),7(8)-bisformylbicyclo[4.3.0]nonane with hydrogen and ammonia in the presence of a hydrogenation catalyst. However, the dialdehyde can also initially be reacted with a primary amine to form a diazomethine and the diazomethine can then be treated with hydrogen and ammonia in the presence of a hydrogenation catalyst. In the context of the invention, this reaction is also referred as to reductive amination.

To form the diazomethine, from 2 to 6 mol, preferably 3 to 4 mol, of a primary amine are added per mole of 3(4),7(8)-bisformylbicyclo[4.3.0]nonane to the hydroformylation mixture which has been worked up. The reaction between the starting materials proceeds even at room temperature and can be accelerated by heating to 20 to 60° C., preferably 30 to 50° C. Suitable primary amines are amines having from 2 to 10 carbon atoms in the molecule, preferably n-butylamine, are used.

The reductive amination of the dialdehyde or the diazomethine is appropriately carried out at temperatures of 60 to 150° C., preferably 80 to 140° C. The hydrogen pressure in the reaction vessel at the reaction temperature is 2 to 12 MPa and particularly 8 to 10 MPa.

The hydrogenation catalysts used are nickel or cobalt, either in the form of Raney nickel or Raney cobalt, or else in the form of corresponding supported catalysts. A preferred catalyst contains from 50 to 60% by weight of nickel on kieselguhr.

Ammonia should appropriately be used in excess. Per mole of formyl group or per mole of diazomethine group, at least 2 mol of ammonia are required and preference is given to using 4 to 10 moles of ammonia.

The reductive amination of the dialdehyde or of the diazomethine may be carried out in the absence of solvents; the end product itself typically acts as a solvent. However, in the case of small batches, it is advantageous to work in a solvent. Particularly good results are achieved when tetrahydrofuran, isobutanol, butanol or isopropanol is used as the solvent.

The mixture of the isomeric diamines is obtained in good yields. Only a small portion of the dialdehydes is converted to higher molecular weight condensation products. They are dissolved in the reaction mixture and do not disrupt the withdrawal of product from the reactor or trouble-free workup of the crude products.

To remove 3(4),7(8)bis(aminomethyl)bicyclo[4.3.0] nonane, the reaction mixture is distilled, preferably under reduced pressure. The compounds are obtained as a colorless liquid which boils, for example, at about 149° C. under a pressure of 5 hPa. The hydrogenation catalyst and the transition metal used in the hydroformylation stage are obtained in the distillation residue and are recovered by known processes.

The reaction product of the hydroformylation of bicyclo[4.3.0]nona-3,7-diene can also first be distilled by conventional processes and reductively aminated as the purified product. Surprisingly, 3(4),7(8)-bisformylbicyclo[4.3.0] nonane can be obtained with high distillative yield in pure form. This is all the more surprising because the prior art points out the thermal lability of dialdehydes with fused alicyclic ring structures. Transition metal, preferably rhodium, and added organophosphorus compounds are obtained in the distillation residue and are recovered by known methods. The subsequent reductive amination of the purified 3(4),7(8)-bisformylbicyclo[4.3.0]nonane is effected as in the case of the reaction of the crude hydroformylation product.

The process according to the invention permits a simple and inexpensive route to 3(4),7(8)-bis(aminomethyl)bicyclo[4.3.0]nonane in high yield and in high purity. The diamine prepared by the process according to the invention can be used in an excellent manner for different applications, for example as a hardener for epoxy resins, as a constituent in polyurethanes and polyamides, and for the preparation of conversion products which are used as additives in fuels and lubricants.

In the following examples, there are described several preferred embodiments to illustrate the invention. However, it is to be understood that the invention is not intended to be limited to the specific embodiments.

EXAMPLES

1. Preparation of 3(4),7(8)-bisformylbicyclo[4.3.0]nonane

A steel autoclave with a magnetic stirrer was initially charged with 1,000 g of bicyclo[4.3.0]nona-3,7-diene of technical quality and 1000 g of toluene. After adding 12.75 g of triphenylphosphine and 50 mg of rhodium in the form of a toluenic solution of rhodium 2-ethylhexanoate having a content of 7,062 mg of Rh/kg, the mixture was heated to 130° C. and treated with synthesis gas under a pressure of 26 MPa. After a reaction time of 8 hours, the hydroformylation reaction was ended.

The organic phase was analyzed by gas chromatography.

GC Analysis (Area Percent without Toluene)

| components in first runnings | 0.2 |
|---|---|
| bicyclo[4.3.0]nona-3,7-diene range | 0.1 |
| components | 4.6 |
| 3(4),7(8)-bisformylbicyclo[4.3.0]nonane | 89.1 |
| triphenylphosphine/triphenylphosphine oxide | 1.2 |
| high boilers | 4.8 |

2. Preparation of 3(4),7(8)-bis(aminomethyl)bicyclo[4.3.0]nonane

The crude 3(4),7(8)-bisformylbicyclo[4.3.0]nonane obtained after the hydroformylation was freed largely of the toluene by distillation on a thin-film evaporator (jacket temperature 140° C., pressure 100 hPa). A residue was obtained which, by gas chromatography analysis, also contained 9.5% components in addition to 6.7% toluene and 83.8% of 3(4),7(8)-bisformylbicyclo[4.3.0]nonane. The residue was subsequently used in the reductive amination.

To this end, 380.3 g of n-butylamine were initially charged into a 2 liter three-neck flask with stirrer, and admixed with 477.5 g of distillation residue at a temperature of 50° C. within 120 minutes. The mixture was stirred at 50° C. for a further two hours, then cooled, and the water phase which occurred (50.4 g) was separated from the organic phase (807.4 g) (Schiff base).

805.0 g of the organic phase and 48.3 g of Ni 52/35—catalyst from Johnson-Matthey plc—were then initially charged in a 3 liter autoclave. After hydrogen had been injected up to a pressure of 1.5 MPa, 340.6 g of ammonia were pumped in. The mixture was then heated to 125° C. and the pressure was adjusted to 10 MPa by feeding further hydrogen. The Schiff base formed beforehand from the reaction between 3(4),7(8)-bisformylbicyclo[4.3.0]nonane and n-butylamine had been converted under these conditions after 6 hours. After the reaction had ended, the reaction mixture was cooled, decompressed and filtered from the catalyst. The reaction product thus obtained was analyzed by gas chromatography.

GC Analysis (Area Percent)

| components of first runnings | 0.1% |
|---|---|
| n-butylamine | 36.2% |
| toluene/methylcyclohexane | 4.5% |
| 3(4),7(8)-bis(aminomethyl)bicyclo[4.3.0]nonane | 51.7% |
| others | 7.5% |

For workup, 721.7 g of the crude 3(4),7(8)-bis(aminomethyl)bicyclo[4.3.0]-nonane were distilled on a column having 4.5 theoretical plates to obtain 281.4 g of main fraction in a boiling range of 148-149° C. at a pressure of 5 hPa with the following composition.

GC Analysis (Area Percent)

| components of first runnings | <0.1% |
|---|---|
| 3(4),7(8)-bis(aminomethyl)bicyclo[4.3.0]nonane | 99.3% |
| others | 0.7% |

The overall yield of 3(4),7(8)-bis(aminomethyl)bicyclo[4.3.0]nonane over all stages is 73.0% of theory based on bicyclo[4.3.0]nona-3,7-diene.

NMR Data $^1$H NMR (500 MHz, DMSO-$d_6$, ppm): 0.57-2.71 (m, 22H CH, $CH_2$ and $NH_2$)

$^{13}$C NMR (125 MHz, DMSO-$d_6$, ppm): 24.48-49.63 (CH and $CH_2$),

GC-MS (PCl): m/z=365 $\{2M.H\}^+$, 239$\{M.C_4H_9\}^+$, 183 $\{M.H\}^+$

IR Data (Diamond ATR-IR Spectroscopy)

ν ($cm^{-1}$) 3369 (w), 3287 (w), 2908 (s), 2852 (s), 1603 (m, br), 1446 (m), 807 (s, br)

| Density at 20° C. | 0.9845 g/cm³ |
|---|---|
| Refractive index $n_D$ at 20° C. | 1.5106 |

The process of the invention opens up an elegant preparative route for 3(4),7(8)-bis(aminomethyl)bicyclo[4.3.0]nonane in high yields. The 3(4),7(8)-bis(aminomethyl)bicyclo[4.3.0]nonane has an alicyclic ring structure with fused rings, which is outstandingly suitable as a hardener for epoxy resins or as a constituent for polyurethanes and polyamides. It can likewise be used to prepare conversion products which are used as additives in fuels and lubricants.

Various modifications of the process may be made without departing from the spirit or scope of the invention and it is to be understood that the invention is intended to be limited only as defined in the appended claims.

What is claimed is:

1. A process for preparing 3(4),7(8)-bis(aminomethyl)bicyclo[4.3.0]nonane by hydroformylating bicyclo[4.3.0]nona-3,7-diene with subsequent reductive amination, comprising reacting bicyclo[4.3.0]nona-3,7-diene with synthesis gas in a homogeneous organic phase in the presence of transition metal compounds of Group VIII of the Periodic Table containing complex-bound organophosphorus compounds, and excess organophosphorus compound, at temperatures of 70 to 160° C. and pressures of 5 to 35 MPa, and then reductively aminating the 3(4),7(8)-bisformylbicyclo[4.3.0]nonane thus obtained to form 3(4),7(8)bis(aminomethyl)bicyclo[4.3.0]nonane.

2. The process of claim 1, wherein the organophosphorus compounds are organic phosphorus (III) compounds selected from the group consisting of triarylphosphines, trialkylphosphines, alkylarylphosphines, alkyl phosphites, aryl phosphites, alkyl diphosphites and aryl diphosphites.

3. The process of claim 2, wherein the triarylphosphine used is triphenylphosphine and the aryl phosphite used is tris(2-tert-butylphenyl)phosphite or tris(2-tert-butyl-4-methylphenyl)phosphite.

4. The process of claim 1, wherein the transition metal compounds of Group VIII of the Periodic Table used are selected from the group consisting of compounds of rhodium, cobalt, iridium, nickel, palladium, platinum, iron and ruthenium.

5. The process of claim 1, wherein the transition metal compounds of Group VIII of the Periodic Table used are compounds of rhodium.

6. The process of claim 1, wherein rhodium is used in a concentration of from 5 to 1000 ppm by weight based on the homogeneous reaction mixture.

7. The process of claim 6, wherein rhodium is used in a concentration of 10 to 700 ppm by weight, based on the homogeneous reaction mixture.

8. The process of claim 1, wherein the molar ratio of rhodium to phosphorus is 1:5 to 1.200.

9. The process of claim 8, wherein the molar ratio of rhodium to phosphorus is 1:10 to 1:100.

10. The process of claim 1, wherein the hydroformylation is performed at temperatures 80 to 150° C., and at pressures of 10 to 30 MPa.

11. The process of claim 1, wherein the reductive amination is performed in the presence of nickel catalysts at temperatures of 60 to 150° C. and at a hydrogen pressure of 2 to 12 MPa.

12. The process of claim 11, wherein the diazomethine formed from 3(4),7(8)-bisformylbicyclo[4.3.0]nonane and a primary amine of 2 to 10 carbon atoms in the molecule is used for the reductive amination.

13. The process of claim 7 wherein rhodium is used at 20 to 500 ppm by weight.

14. The process of claim 10 wherein the temperature is 90 to 140° C. and the pressure is 20 to 30 MPa.

15. 3(4),7(8)-bis(aminomethyl)bicyclo[4.3.0]nonane.

* * * * *